US012357714B2

(12) United States Patent
Sure et al.

(10) Patent No.: US 12,357,714 B2
(45) Date of Patent: Jul. 15, 2025

(54) SYSTEM AND METHOD FOR SANITIZING AN OBJECT

(71) Applicant: HONEYWELL INTERNATIONAL INC., Charlotte, NC (US)

(72) Inventors: Anita Sure, Charlotte, NC (US); Gowtham Kumar Vankayala, Charlotte, NC (US); Harish Nagarajaiah, Charlotte, NC (US); Pramod Kumar T P, Charlotte, NC (US); Tilak Ravi Krishnaswamy, Charlotte, NC (US); Venugopal Krishnappa, Charlotte, NC (US); Krishna Prasad Sabeson, Charlotte, NC (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 932 days.

(21) Appl. No.: 17/450,512

(22) Filed: Oct. 11, 2021

(65) Prior Publication Data

US 2022/0118134 A1   Apr. 21, 2022

(30) Foreign Application Priority Data

Oct. 16, 2020  (IN) .............................. 202011045193

(51) Int. Cl.
*A61L 2/00*  (2006.01)
*A61L 2/10*  (2006.01)
(Continued)

(52) U.S. Cl.
CPC ............. *A61L 2/10* (2013.01); *A61L 2202/11* (2013.01); *A61L 2202/122* (2013.01); *A61L 2202/14* (2013.01)

(58) Field of Classification Search
CPC .......... A61L 2/08; A61L 2/10; A61L 2202/23; F21V 7/08; F21V 7/0016
(Continued)

(56) References Cited

U.S. PATENT DOCUMENTS

| 5,326,542 A | 7/1994 | Sizer et al. |
| 7,791,044 B1 | 9/2010 | Taylor et al. |

(Continued)

OTHER PUBLICATIONS

IN Office Action, IN Application No. 202011045193, India Patent Office, May 9, 2022 (5 pgs).

*Primary Examiner* — Monzer R Chorbaji
(74) *Attorney, Agent, or Firm* — Seager, Tufte & Wickhem, LLP

(57) ABSTRACT

Systems and method for sanitizing a system using ultraviolet light. A system for sanitizing an object may comprise a housing defining a tunnel and a conveyor movable in a first direction to move an object through the tunnel from the entrance opening to the exit opening. A plurality of ultraviolet (UV) light sources may be positioned about the tunnel. A plurality of reflectors each may extend partially around a corresponding UV light source. Each reflector may be configured to collect UV light emission from the corresponding UV light source and provide a directional projection of UV light into the tunnel. At least one reflector may provide a directional projection of UV light that is angularly offset toward the exit opening of the tunnel and at least one reflector may provide a directional projection of UV light that is angularly offset toward the entrance opening of the tunnel.

20 Claims, 10 Drawing Sheets

(51) Int. Cl.
*G01N 21/00* (2006.01)
*G01N 23/00* (2006.01)

(58) Field of Classification Search
USPC ...... 422/22, 24; 250/453.11, 454.11, 455.11, 250/492
See application file for complete search history.

(56) References Cited

U.S. PATENT DOCUMENTS

| | | |
|---|---|---|
| 8,213,570 B2 | 7/2012 | Panesar et al. |
| 8,617,464 B2 | 12/2013 | Kerr |
| 2007/0110860 A1 | 5/2007 | Fink et al. |
| 2011/0162226 A1 | 7/2011 | Witt |
| 2017/0209607 A1 | 7/2017 | Safraoui |
| 2019/0338919 A1* | 11/2019 | Wilk .................... F21V 7/0016 |
| 2020/0297004 A1 | 9/2020 | Alzeer et al. |

* cited by examiner

US 12,357,714 B2

SYSTEM AND METHOD FOR SANITIZING AN OBJECT

CROSS-REFERENCE TO RELATED APPLICATIONS

This application claims priority pursuant to 35 U.S.C. 119(a) to India Patent Application No. 202011045193, filed Oct. 16, 2020, which application is incorporated herein by reference in its entirety.

TECHNICAL FIELD

The disclosure generally relates to ultraviolet light sanitization systems, and more particularly to systems and methods for sanitizing an object.

BACKGROUND

Some conventional ultraviolet (UV) light sanitization systems include a sanitizing tunnel through which objects are passed. The sanitizing tunnel is typically flooded with ultraviolet light by numerous UV lamps, often in a fairly non-efficient manner. This can result in an excessive number of UV lamps, which can increase the initial cost of the sanitization system, increase the cost of maintaining the sanitization system, and increase the energy required to operate the sanitization system. Moreover, the UV light, which is typically flooded into the sanitization tunnel, results in some UV light being directed out an inlet and/or outlet of the sanitizing tunnel, which can create a safety hazard for nearby operators. What would be desirable is a system and method that reduced the number of UV lamps that are required by directing the UV light in a controlled and efficient manner to targets all surfaces of an object while limit human exposure to the UV light.

SUMMARY

This disclosure generally relates to sanitization systems, and more particularly to systems and methods for sanitize an object. In a first example, a system for sanitizing an object may include a housing defining a sanitization tunnel. The tunnel may extend between an entrance opening and an exit opening. The tunnel may also have a first lateral side, a second lateral side, a top side, and a bottom side. The system may further include a conveyor (e.g. conveyor belt or the like) movable in a first direction to move an object placed on the conveyor through the tunnel from the entrance opening to the exit opening, a plurality of ultraviolet (UV) light sources positioned about the tunnel with at least one of the plurality of UV light sources positioned along each of the first lateral side, the second lateral side, the top side, and the bottom side of the tunnel. Each of the plurality of UV light sources provide a corresponding UV light emission, and a plurality of reflectors each extending partially around a corresponding UV light source. Each of the plurality of reflectors is configured to collect UV light emission from the corresponding UV light source and provide a controlled directional projection of UV light into the tunnel. At least one reflector of the plurality of reflectors may provide a directional projection of UV light that is angularly offset toward the exit opening of the tunnel relative to a plane that is normal to the first direction of the conveyor, and at least one reflector of the plurality of reflectors may provide a directional projection of UV light that is angularly offset toward the entrance opening of the tunnel relative to a plane that is normal to the first direction of the conveyor.

In some cases, each of the plurality of reflectors may be configured to provide a directional projection of UV light that does not intersect with the entrance opening or the exit opening of the tunnel. In some cases, at least one reflector of the plurality of reflectors may provide a directional projection of UV light that is angularly offset by an angle in a range of 1° to about 15° toward the exit opening of the tunnel relative to a normal to the first direction of the conveyor. In some cases, at least one reflector of the plurality of reflectors may provide a directional projection of UV light that is angularly offset by an angle in a range of 1° to about 15° toward the entrance opening of the tunnel relative to the normal to the first direction of the conveyor.

In some cases, at least one of the plurality of UV light sources may be elongated and produce an elongated projection of UV light.

In some cases, each of the plurality of reflectors may be configured to collect UV light emission from a corresponding UV light source and provide a directional projection of UV light that has a divergence angle that is less than 20 degrees.

In some cases, at least two of the plurality of UV light sources may be positioned along each of the first lateral side, the second lateral side, the top side, and the bottom side of the tunnel. In some cases, at least two of the plurality of UV light sources may be spaced from one another in the first direction and positioned along each of the first lateral side, the second lateral side, the top side, and the bottom side of the tunnel.

In some cases, the system may further include a controller operatively coupled to the plurality of UV light sources, wherein the controller may be configured to turn the plurality of UV light sources ON and OFF, and also to set an intensity level of at least one of the plurality of UV light sources.

In some cases, the controller may be operatively coupled to a motor driving the conveyor, and is configured to control a speed of the motor and thus a speed of the conveyor.

In some cases, the controller may be configured to control the intensity level of at least one of the plurality of UV light sources based on the speed of the conveyor.

In some cases, the controller may be configured to control the intensity level of at least one of the plurality of UV light sources based on a size of the object being sanitized.

In some cases, the system may further include a heater configured to increase a temperature within the tunnel.

In another example, a system for sanitizing an object may include a housing defining a tunnel, where the tunnel extends between an entrance opening and an exit opening. The tunnel also has a first lateral side, a second lateral side, a top side, and a bottom side, a conveyor movable in a first direction to move an object placed on the conveyor through the tunnel from the entrance opening to the exit opening. A plurality of ultraviolet (UV) light source assemblies are positioned about the tunnel with at least one of the plurality of UV light source assemblies along each of the first lateral side, the second lateral side, the top side, and the bottom side of the tunnel. Each of the plurality of UV light source assemblies providing a directional projection of UV light into the tunnel. At least one of the plurality of ultraviolet (UV) light source assemblies may provide a directional projection of UV light that is angularly offset toward the exit opening of the tunnel relative to a plane that is normal to the first direction of the conveyor, and at least one of the plurality of ultraviolet (UV) light source assemblies may provide a directional projection of UV light that is angularly offset toward the entrance opening of the tunnel relative to a plane that is normal to the first direction of the conveyor.

In some cases, the angularly offset toward the entrance opening of the tunnel may be in a range of 1° to about 15°, and the angularly offset toward the exit opening of the tunnel may be in a range of 1° to about 15°.

In some cases, each of the plurality of ultraviolet (UV) light source assemblies may be configured to provide a directional projection of UV light that does not intersect with the entrance opening or the exit opening of the tunnel.

In some cases, each of the plurality of ultraviolet (UV) light source assemblies may include a UV light source and a reflector.

In some cases, the system may further include a heater configured to increase a temperature within the tunnel.

In another example, a method for sanitizing an object includes conveying the object through a tunnel, where the tunnel has an entrance opening, an exit opening, a first lateral side, a second lateral side, a top side, and a bottom side. The example method includes projecting UV light having a divergence angle of less than 10 degrees from each of a plurality of UV light sources onto the object from each of the first lateral side, the second lateral side, the top side, and the bottom side. Projecting the UV light may include projecting UV light having a divergence angle of less than 10 degrees that is angularly offset toward the exit opening of the tunnel relative to a plane that is normal to a direction of conveyance of the object, and projecting UV light having a divergence angle of less than 10 degrees that is angularly offset toward the entrance opening of the tunnel relative to a plane that is normal to the direction of conveyance of the object. In some cases, substantially no UV light may be projected onto the entrance opening or the exit opening of the tunnel.

In some cases, the method may further include heating the tunnel while sanitizing the object.

The preceding summary is provided to facilitate an understanding of some of the features of the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following detailed description of various embodiments in connection with the accompanying drawings, in which.

Figure 1A:
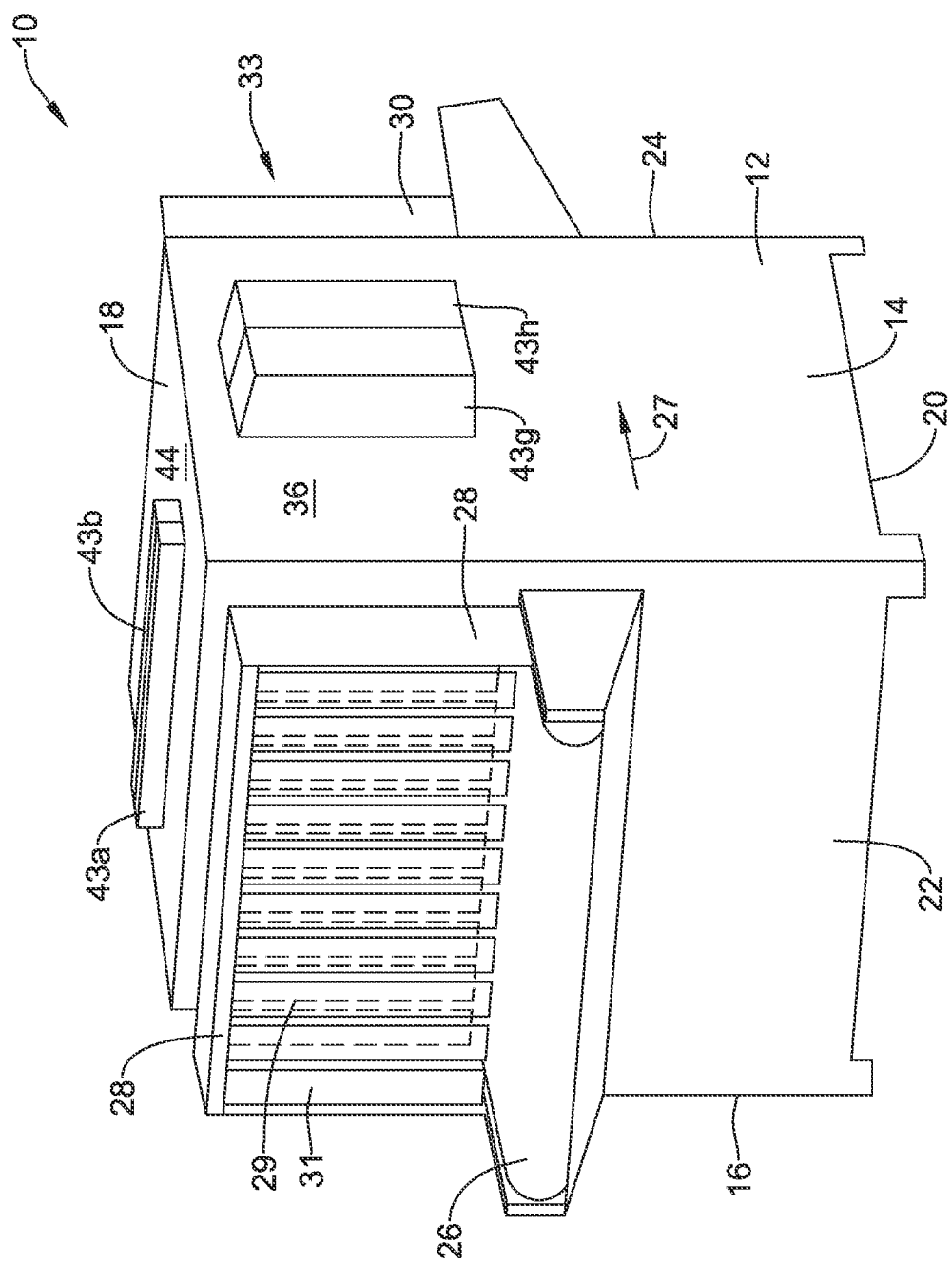
FIG. 1A is perspective view of an illustrative sanitization tunnel device.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DESCRIPTION

The following detailed description should be read with reference to the drawings in which similar elements in different drawings are numbered the same. The description and the drawings, which are not necessarily to scale, depict illustrative embodiments and are not intended to limit the scope of the disclosure. The illustrative embodiments depicted are intended only as exemplary. Some or all of the features of any illustrative embodiment can be incorporated into other illustrative embodiments unless clearly stated to the contrary.

Figure 1B:
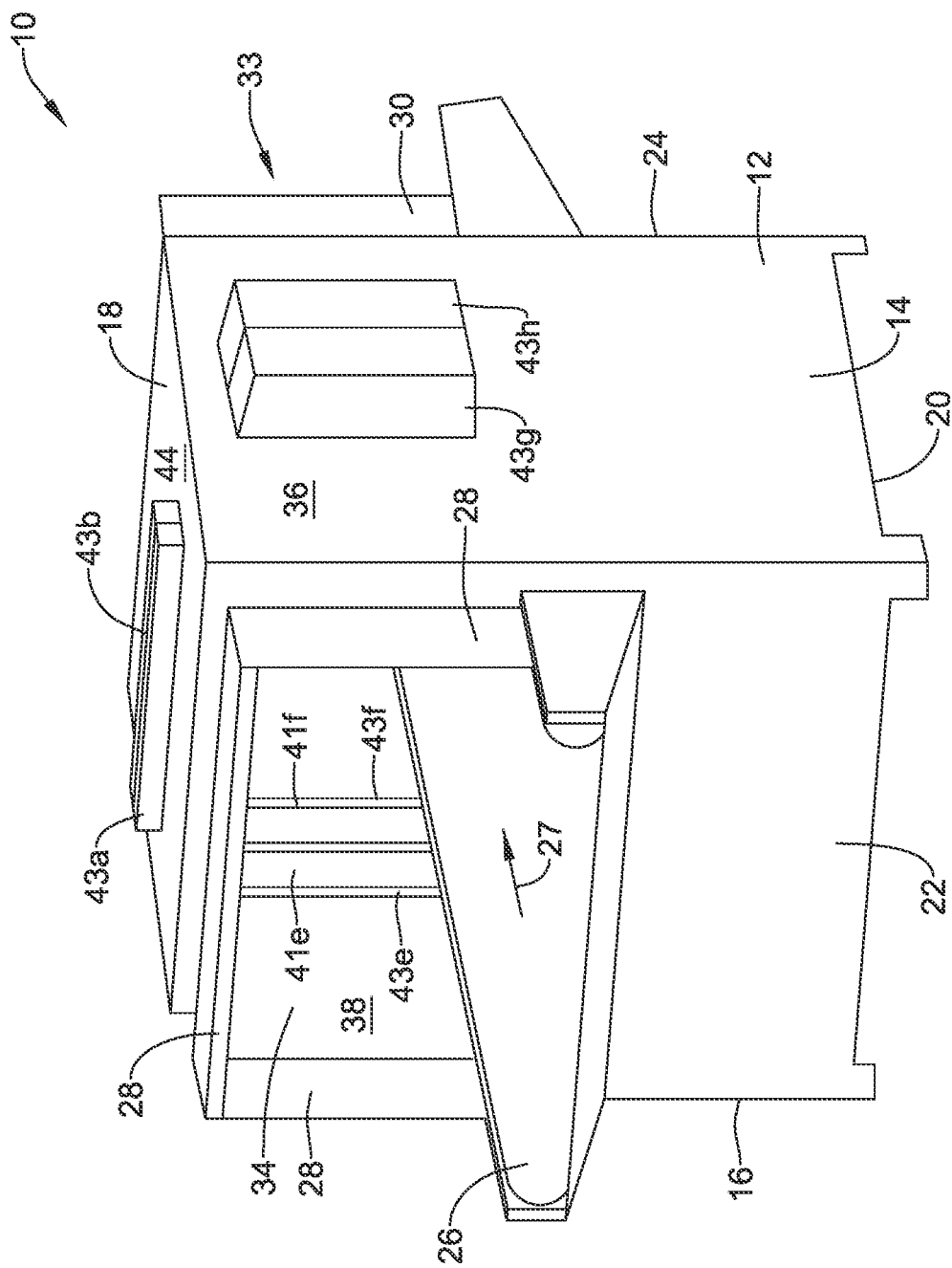
FIG. 1B is a perspective view of the illustrative sanitization tunnel device with portions removed.

FIG. 1A is a perspective view of an illustrative sanitization tunnel device 10 and FIG. 1B is a perspective view of the illustrative sanitization tunnel device 10 with UV shields removed. The sanitization tunnel device 10 may utilize ultraviolet (UV) light to sanitize or disinfect objects or air passing through the sanitization tunnel device 10. In some cases, the sanitization tunnel device 10 may be utilized to disinfect baggage (e.g., at an airport or other transportation hub) or parcels at a distribution facility. These are just some examples. The sanitization tunnel device 10 may be utilized in any situation where it is desired to disinfect or sanitize an object. Generally, UV light may be broadly defined as light having a wavelength in the range of about 10 to 400 nanometers (nm) on the electromagnetic spectrum. The broad range can be broken down into a number of different ranges. In one example, UV light can be categorized as UVA having a wavelength of about 315 to 400 nm, UVB having a wavelength of about 280 to 315 nm, and UVC having a wavelength in the range of about 100 to 280 nm. UV light falling within the UVC range is most often used for disinfection and sanitization purposes. More particularly, UV lights emitting light within about 230 to 280 nm are most commonly used for sanitization purposes. However, UVC light (and other short-wave UV light) can be damaging to the skin and eyes of people.

The effectiveness of UV light as a disinfectant may be determined, at least in part, by a dosage of the UV light. For example, the dosage may include a length of time a pathogen, microorganism, etc. is exposed to the UV light, the intensity of the UV light, and/or the wavelength of the UV light. In one illustrative example, to deactivate the coronavirus which causes coronavirus disease 2019 (COVID-19), a dosage of about or at least 22 millijoules (mJ) per square centimeter ($cm^2$) may be required. In one example, the dosage received by the object to be disinfected/sanitized may be determined by multiplying the UV intensity (Watts per area) by the exposure time. It is contemplated the UV dosage may be specified based on the dosage required to deactivate one or more pathogens.

The illustrative sanitization tunnel device 10 may include a housing 12. The housing 12 may generally be a six-sided shape having a first side 14, a second side 16, a top 18, a bottom 20, a front (or first end) 22 and a back (or second end) 24, as depicted in the views of FIGS. 1A and 1B. The terms top, bottom, back, front, first, and second are relative terms used merely to aid in discussing the drawings, and are not meant to be limiting in any manner. A conveyor (e.g. conveyor belt, rollers or other conveying) 26, movable in a first direction 27 to move an object from the front 22 to the back 24 of the sanitization tunnel device 10, may extend through the housing 12. The conveyor 26 is positioned between the top 18 and bottom 20 of the housing 12. In some cases, the conveyor 26 may have a length that is longer than a length of the housing 12 (e.g., from the front 22 to the back 24) so that the conveyor 26 extends laterally beyond the front 22 and/or back 24 of the housing 12. Guides or panels 28 may extend away from the front 22 of the housing 12 adjacent to the conveyor 26. Similarly, guides or panels 30 may extend away from the back 24 of the housing 12 adjacent to the conveyor 26. The panels 28, 30 may generally surround three sides of the conveyor 26 to guide objects into and/or out of a tunnel 32 defined by the housing 12. The guides 28, 30 may be formed from a UV blocking material so as to protect a user or operator of the sanitization tunnel device 10 from UV rays that may escape from the tunnel 32 (e.g. by reflection or the like). The sanitization tunnel device 10 may further include a first layer of light blinders 29 and a second layer of light blinders 31 adjacent to the front 22 of the housing 12. The first layer of light blinders 29 may be formed from a material or coated with a material having properties to protect against UV light. The first layer of blinders 29 may be positioned closer to the UV light source than the second layer of blinders 31. The second layer of blinders 31 may be laterally spaced from the first layer of blinders 29. The first and second layers of blinders 29, 31 may be formed from a plurality of flexible flaps which allow an object to pass through. The plurality of flaps may be positioned adjacent to one another to help ensure minimal UV light escapes from the tunnel 32. While not explicitly shown, the back 24 of the housing 12 may include a similarly structured dual layer of blinders. It is contemplated that the blinders 29,31 and panels 28, 30 cooperate to reduce the amount of UV light an operator or other personnel close to the sanitization tunnel device 10 may be exposed to.

The tunnel 32 may be configured to transport an object to be disinfected/sanitized from the front 22 to the back 24 of the housing 12 via the conveyor 26. In the example show, the tunnel 32 extends between an entrance opening 34 formed in the front 22 of the housing 12 and an exit opening 33 formed in back 24 of the housing 12. The tunnel 32 may include a first lateral side defined by a first side wall 36 of the housing 12, a second lateral side defined by a second side wall 38 (see FIG. 1B) of the housing 12, a top side defined by a top wall 44 of the housing 12 and a bottom side defined by the conveyor 26. The first side wall 36 and the second side wall 38 may extend generally parallel to one another along opposite lateral sides of the tunnel 32. Similarly, the top wall 44 and the conveyor 26 may extend generally parallel to one another along opposite sides of the tunnel 32. The first and second side walls 36, 38 may extend orthogonal to the top wall 44 and the conveyor 26 to define a tunnel 32 having a generally rectangular cross-section. The general rectangular cross-section is only illustrative, and other shapes are contemplated. The conveyor 26 is configured to transport an object placed on the conveyor 26 through the tunnel 32 from the entrance opening 34 to the exit opening 33. The dimensions (e.g., height, width, length) of the tunnel 32 may be selected based on the largest object expected to be disinfected/sanitized within the sanitization tunnel device 10.

Figure 2:
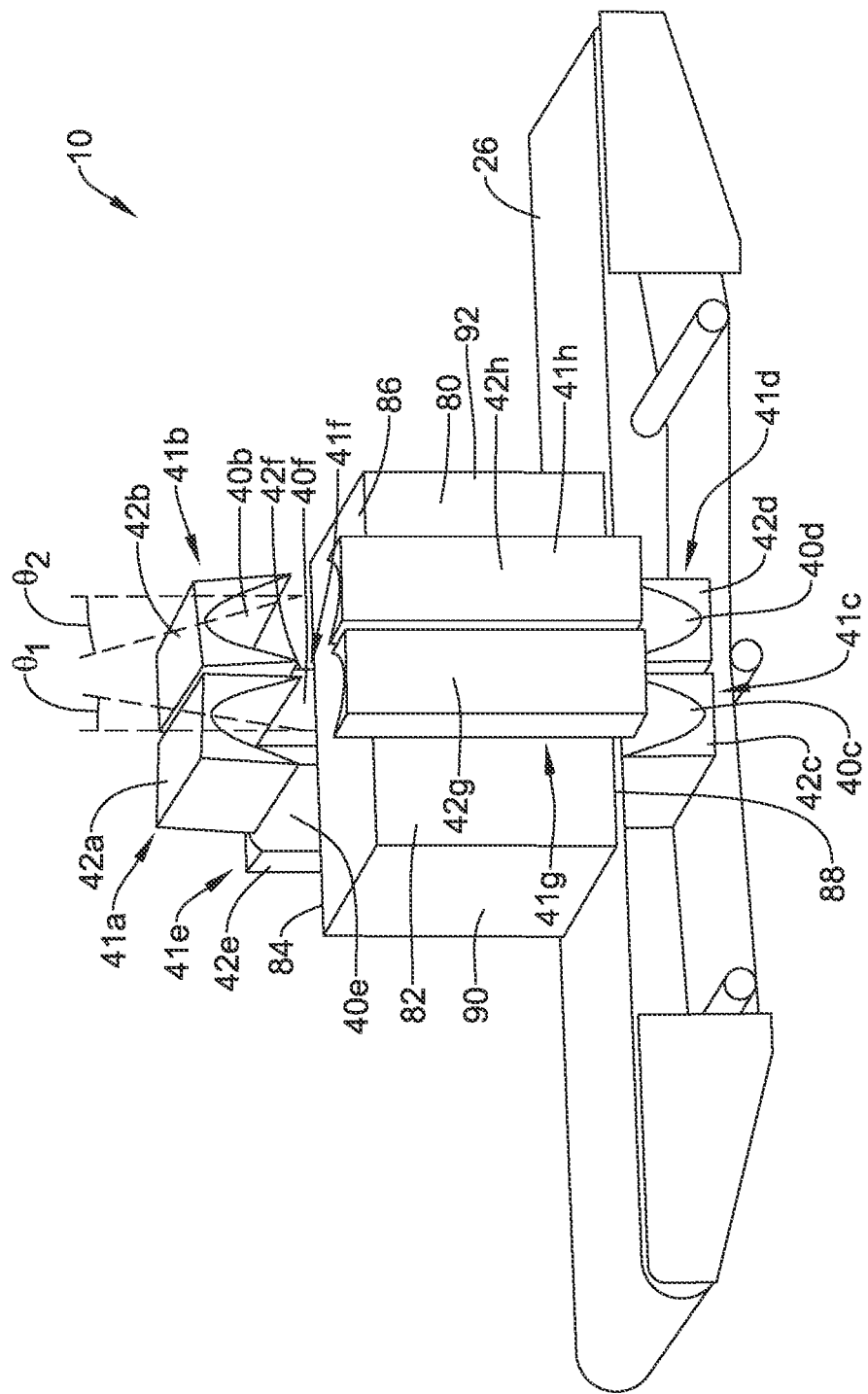
FIG. 2 is a perspective view of a portion of the illustrative sanitization tunnel device of FIG. 1.

Referring additionally to FIG. 2, which illustrates the sanitization tunnel device 10 with the housing 12 removed. As can be seen, the illustrative sanitization tunnel device 10 includes one or more ultraviolet (UV) light sources 40a, 40b, 40c, 40d, 40e, 40f (collectively, 40) each configured to provide a UV light emission. The UV light sources 40 may include, but are not limited to, mercury vapor lamps or UV light emitting diodes (LEDs). Other UV light sources 40 may be used, as desired. The UV light sources 40 may be positioned such at least one light source is along each of the first lateral side, the second lateral side, the top side, and the bottom side of the tunnel 32. In some cases, two or more UV light sources 40 may be positioned along each of the first lateral side, the second lateral side, the top side, and the bottom side of the tunnel 32. When two or more UV light sources 40 are provided along one or more sides of the tunnel 32, the two or more UV light sources 40 may be laterally spaced in the direction of the conveyor 26 as shown. It is further contemplated that each of the first lateral side, the second lateral side, the top side, and the bottom side of the tunnel 32 need not have the same number of UV light sources 40.

Each of a plurality of reflectors 42a, 42b, 42c, 42d, 42e, 42f, 42g, 42h (collectively, 42) may extend at least partially around a corresponding UV light source 40. A reflector 42 and its corresponding UV light source 40 may be considered to form a UV light source assembly 41a-h (collectively, 41). In some embodiments, the UV light source assemblies 41 may be positioned within a recess 43a, 43b, 43e, 43f 43g, 43h formed in the tunnel walls 36, 38, 44 of the housing 12. However, this is not required. In some cases, the UV light source assemblies 41 may be fixedly or removably coupled within the tunnel 32.

In some embodiments, the UV light sources 40 may be positioned within a cavity 46 (see, for example, FIG. 3) of a corresponding reflector 42. For example, and while not explicitly shown, UV light sources 40 are positioned within each of the reflectors 42g, 42h positioned adjacent to the first side 14 of the housing 12 (see FIG. 2). Thus, the sanitization tunnel device 10 may include a same number of UV light sources 40 as reflectors 42. Each reflector 42 may be configured to collect UV light emission from a corresponding UV light source 40 and provide a directional projection of the UV light into the tunnel 32, as will be described in more detail herein.

Figure 3:
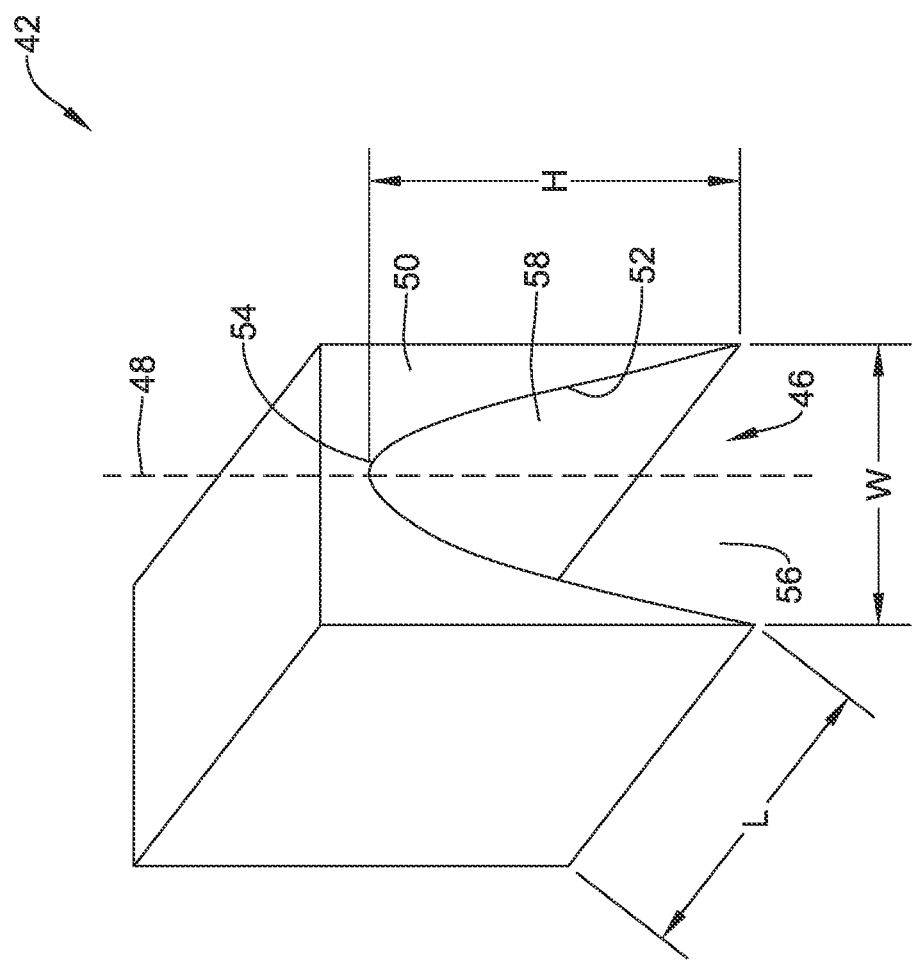
FIG. 3 is a perspective view of an illustrative reflector.

It is contemplated that a variety of different UV light source 40 arrangements may be utilized. In some cases, the UV light sources 40 may be elongated tubular light source which spans a length L (see FIG. 3) of the reflector 42. In other cases, the UV light sources 40 may be an elongated tubular light source which has a length less than a length L of the reflector 42. In yet other examples, the UV light sources 40 may include one or more discrete light sources within each reflector 42. For example, in some cases a UV light source 40 may be positioned centrally along the length L of the reflector 42. In other cases, two or more UV light sources 40 may be uniformly or eccentrically spread along the length L of the reflector 42. Rather than using an elongated reflector as shown in FIG. 3, it is contemplated that a reflector may be configured to accommodate a discrete light source such as a UV LED, and may extend symmetrically around the discrete light source much like a reflector used in a flashlight. It is contemplated that a combination of UV light source types may be utilized, as desired.

FIG. 2 further illustrates an object 80 to be disinfected/sanitized positioned on the conveyor 26. This illustrative object 80 is generally shown as a six-sided shape having a first side 82, a second side 84, a top 86, a bottom 88, a front (or first end) 90 and a back (or second end) 92. The terms top, bottom, back, front, first, and second are relative terms used merely to aid in discussing the drawings, and are not meant to be limiting in any manner. The bottom 88 of the object 80 may rest on the conveyor 26. While the object 80 is illustrated as having a generally rectangular prism or box like shape with six distinct planes, objects to be disinfected/sanitized within the sanitization tunnel device 10 are not so limited. It is contemplated that any shape object that is sized to pass through the tunnel 32 may be disinfected utilizing the sanitization tunnel device 10.

FIG. 3 illustrates a perspective view of an illustrative reflector 42 having a body 50. In the illustrative embodiment, the body 50 has an outer profile generally in the shape of a rectangular prism. However, this is not required. The outer profile can vary, as desired. For example, in some cases, the body 50 may be formed from a bent or curved sheet such that the inner and outer profiles are the same or similar. In the example show, a cavity 46 is formed in and/or by the body 50 of the reflector 42. The cavity 46 extends from a first closed end 54 to a second open end 56. Additionally, the cavity 46 may include an open front end 58 and an open back end (not explicitly shown), but this is not required. In the illustrated example, the cavity 46 may have a length L extending from the front opening 58 to the back opening in the range of about 900 to about 1100 millimeters (mm), a height H extending from the first closed end 54 to the second open end 56 in the range of about 133 to about 143 mm, and a width W of the second open end 56 in the range of about 120 to about 130 mm. It is contemplated that the length L, height H, and width W may be varied according to the size of the tunnel 32 and/or to achieve a desired beam divergence angle within the tunnel 32. The height H may be increased to achieve a lower beam divergence angle. In a particular example, a reflector 42 may have a length L of about 1000 mm, a height H of about 138 mm, a width W of about 125 mm.

The cavity 46 may be structured such that the width W increases from the first closed end 54 to the second open end 56. In the illustrated embodiment, the cross-section of the cavity 46 may have a generally parabolic cross-sectional shape. Said differently, the cavity 46 is shaped such that an inner surface 52 of the body 50 has a parabolic cross-sectional shape. However, this is not required. Other cross-sectional shapes may be used as desired. For example, the cavity 46 may take a cross-sectional shape where the width increases from the first closed end 54 to the second open end 56 including, but not limited, triangular, hemispherical, etc. In some cases, the cavity 46 and/or inner surface 52 may be symmetric about a central vertical plane or an axis of symmetry 48 which extends along the length L of the reflector 42.

Figure 4:
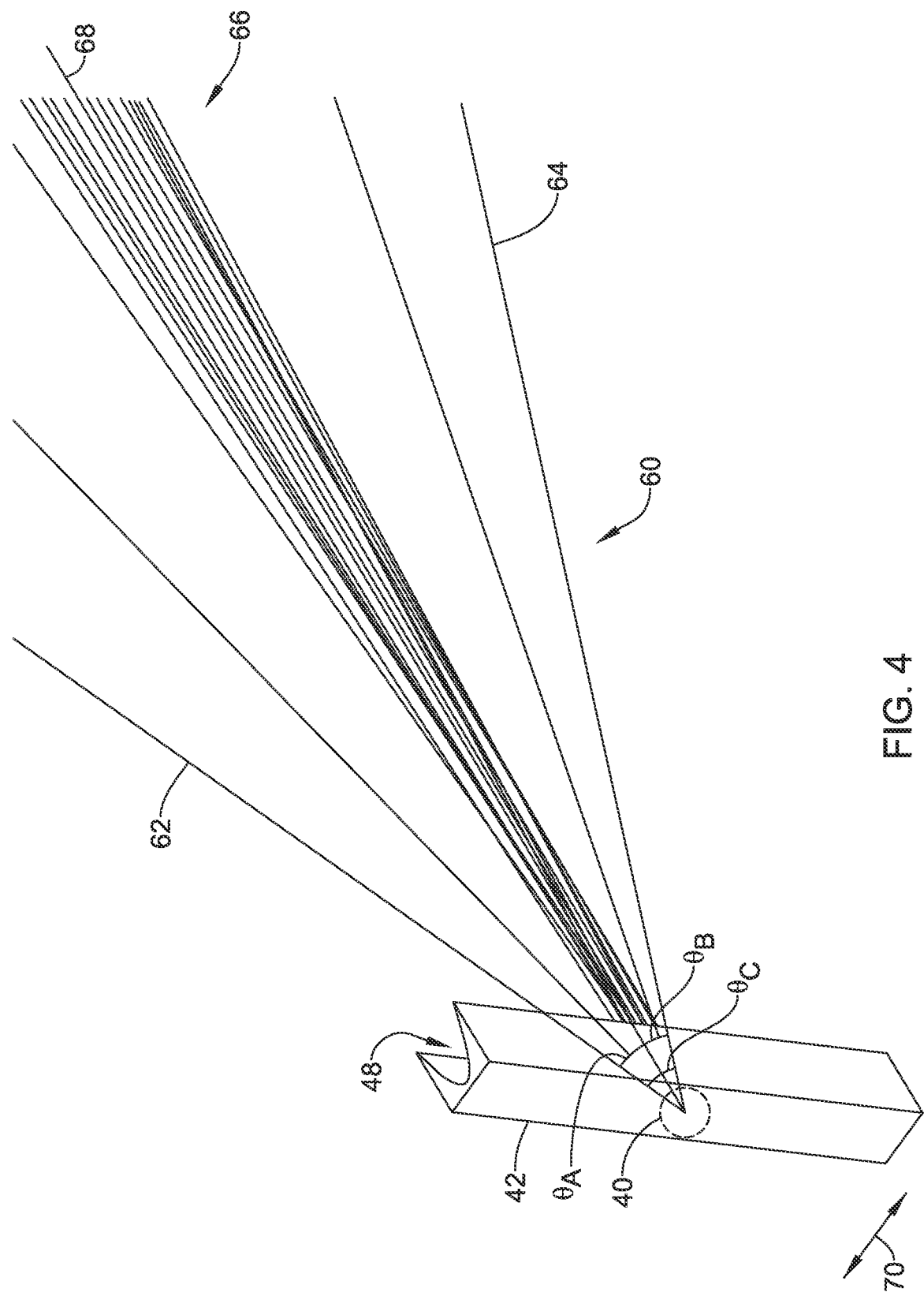
FIG. 4 is a schematic view of a projection of UV light from a UV light source and reflected by the reflector.

The inner surface 52 of the body 50 may form a reflective surface for directing the UV light emission from a corresponding UV light source in a desired direction and/or pattern, and with a desired beam divergence. In some cases, the shape of the inner surface 52 and/or the cavity 46 of the reflector 42 may be configured to collect UV light emission from a corresponding UV light source 40 and provide a corresponding directional projection of UV light. FIG. 4 illustrates a schematic view of a projection of UV light 60 from a centrally located discrete UV light source 40 reflected by the reflector 42. The UV light 60 may extend from a first outer most beam edge 62 to a second outermost beam edge 64. The UV light 60 may be most concentrated in a central region 66 and becoming less concentrated or have less intensity towards the first and/or second outermost beam edges 62, 64. The inner surface 52 of the reflector 42 may be sized and shaped to control the directional projection of the outermost beam edges 62, 64 of the UV light emission 60 in a width direction 70 relative to a central axis 68 and/or the central vertical plane 48 of the reflector 42. The angle $\Theta_A$ between the first outermost beam edge 62 and the central axis 68 of the UV light emission 60 represents a degree of directional projection in a first direction while the angle $\Theta_B$ between the second outermost edge 64 and the central axis 68 of the UV light emission 60 represents a degree of directional projection in a second direction. It is contemplated that when the cavity 46 is symmetrical about the central vertical plane 48, the first and second angles $\Theta_A$, $\Theta_B$ may be the same. The reflector 42 may be configured to provide a directional projection of UV light 60 that has a divergence angle $\Theta_C$, which is the sum of the first and second angles $\Theta_A$, $\Theta_B$. In some cases, the divergence angle $\Theta_C$ may be 10° or less, 20° or less, 30° or less, or 45° or less. However, other divergence angles $\Theta_C$ may be used based on the size of the tunnel 32. In some cases, the divergence angle $\Theta_C$ may be 180° or less or greater than 180°. It is contemplated that controlling the divergence angle $\Theta_C$ may control a spread and concentration of the UV light 60 within the tunnel.

Rather than using an elongated reflector as shown in FIGS. 3-4, it is contemplated that a reflector may be configured to accommodate a discrete light source such as a UV LED, and may extend symmetrically around the discrete light source much like a reflector used in a flashlight. It is contemplated that a combination of UV light source types may be utilized, as desired.

Figure 5:
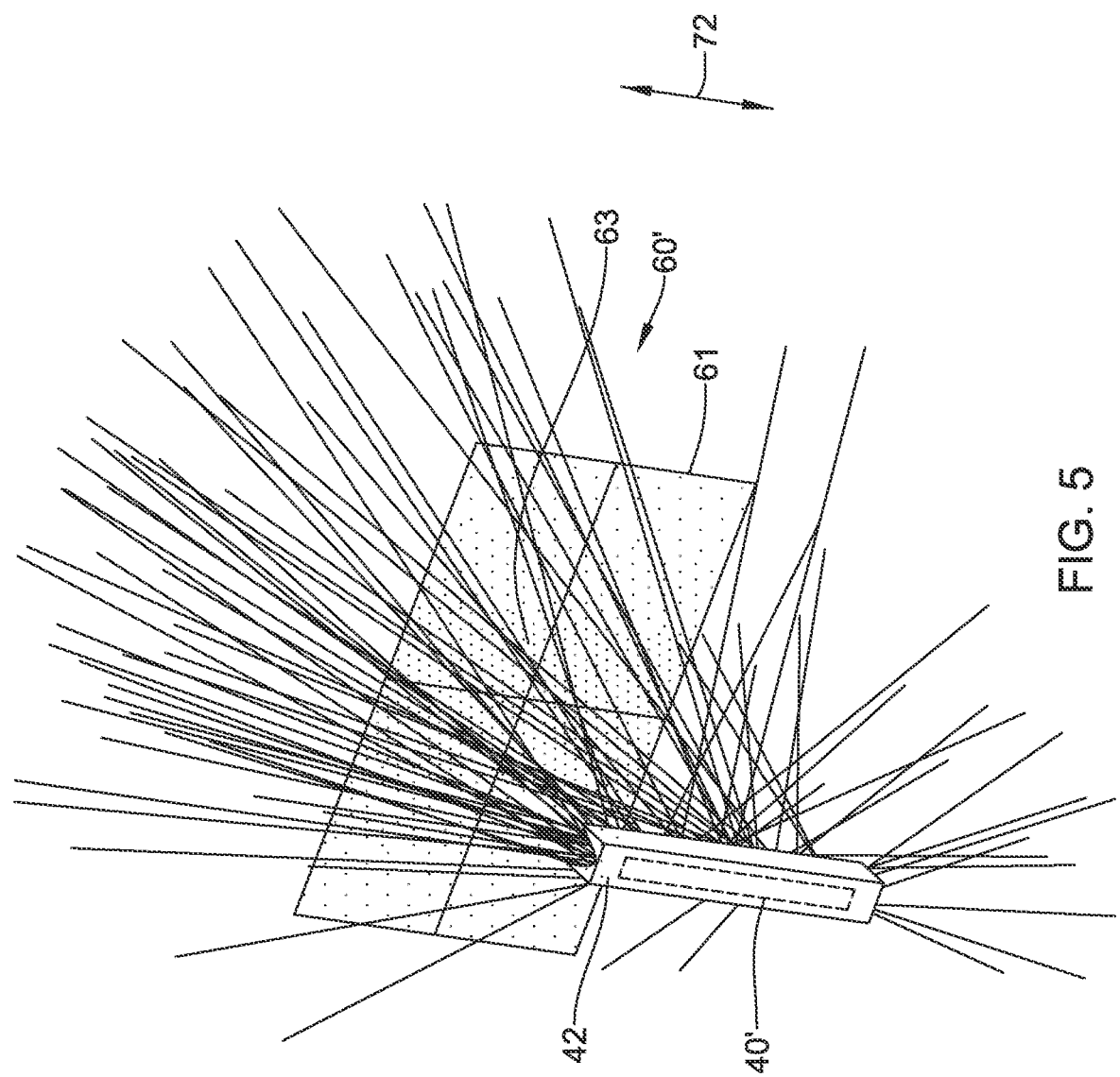
FIG. 5 is another schematic view of a projection of UV light from a UV light source and reflected by the reflector.

FIG. 5 is a schematic view of a projection of UV light 60' emitted from an elongated UV light source 40' and reflected by the reflector 42. The elongated UV light source 40' extends longitudinally along a length of the reflector 42. In such an instance, the UV light source 40' may produce an elongated directional projection of UV light 60'. Generally, the elongated directional projection of UV light 60' may resemble a triangular prism. Compared to the directional projection of UV light 60 produced by the discrete UV light source 40 of FIG. 4, the elongated UV light source 40' may produce a directional projection of UV light that spans a greater distance in the length direction 72. However, it is contemplated that when the shape of the reflector 42 remains the same, the divergence angle $\Theta_C$ for an elongated UV light source 40' would be the same as that of the discrete UV light source.

FIG. 5 further illustrates a heat map 61 of the irradiance received at a distance of one meter. As the reflector directs substantially all (defined here as greater than 90 percent of the light emission from the light source) of the UV light 60' within a defined divergence angle and to a generally central location, the central region 63 is illustrated as having the darkest shading or the most irradiation. As the object 80 moves along the conveyor each side of the object 80 would pass through this most concentrated area of UV light.

Returning back to FIG. 2, the UV light sources 40 and the reflectors 42 are positioned to illuminate the tunnel 32 such that at least one UV light source 40 is positioned along each of the first lateral side, the second lateral side, the top side, and the bottom side of the tunnel 32. Each of the plurality of reflectors 42 may be positioned to provide a directional projection of UV light with a divergence angle that does not intersect with the entrance opening 34 or the exit opening of the tunnel 32. This may help protect workers nearby the sanitization tunnel device 10 from being exposed to the UV light.

In some cases, the reflectors 42g, 42h along the first lateral side of the tunnel 32 and the reflectors 42e, 42f along the second lateral side of the tunnel 32 are positioned such that the central vertical plane 48 of the reflectors extend in a plane generally parallel to the front 22 and/or back 24 of the housing 12. Such an orientation may provide a directional projection of UV light oriented towards the first and second sides 82, 84 of the object 80 to be disinfected/sanitized. Similarly, in some cases, the reflectors 42a, 42b along the top side of the tunnel 32 and the reflectors 42c, 42d along the bottom side of the tunnel 32 are positioned such that the central vertical plane 48 of the reflectors extends in a plane generally parallel to the front 22 and/or back 24 of the housing 12. Such an orientation may provide a directional projection of UV light oriented towards the top and bottom sides 86, 88 of the object 80 to be disinfected/sanitized. The reflectors 42a-h are positioned so that overall they are generally centered along a length of the tunnel 32. For example, the exact center of the tunnel 32 may fall between laterally spaced pairs of UV light sources 40. This may help minimize the UV light directed towards the entrance opening 34 and the exit opening of the tunnel 32.

It is contemplated that at least one of the plurality of reflectors 42 is positioned such that the central vertical plane 48 is not parallel with the front 22 and/or back 24 of the housing 12. For example, at least one reflector 42 may be oriented such that the central vertical plane 48 is angled towards the entrance opening 34 of the tunnel 32. For example, in FIG. 2, reflector 42a is shown angled such that the central vertical plane 48 is positioned at an angle $\Theta_1$ relative to the plane of the entrance opening 34. This angle $\Theta_1$ may generally be in the range of about 1° to about 15°. In some cases, the angle $\Theta_1$ may be about 3°. The angle $\Theta_1$ may be sufficient to provide a directional projection of UV light that is angularly offset toward (or directed toward) the entrance opening 34 of the tunnel 32 relative to a plane that is normal to the movement direction provided by the conveyor 26. In such an instance, this angled directional projection of UV light may direct some of the UV light towards the back side 92 of the object 80 as the back side of the object passes the reflector 42a while also directing UV light towards the top side 86 of the object 80. The reflector 42a may be configured to provide a directional projection of UV light that has a direction and a divergence angle such that substantially no UV light (defined as less than 10 percent of the light emission of the corresponding light source) is projected onto the entrance opening or the exit opening of the tunnel. "Projected onto" means the light that is projected by the light source/reflector and does not include UV light that may be reflected off of the object or other surfaces in the tunnel.

Additionally, or alternatively, at least one reflector 42 may be oriented such that the central vertical plane 48 is angled towards the exit opening of the tunnel 32. For example, in FIG. 2, reflector 42b is angled such that the central vertical plane 48 is positioned at an angle $\Theta_2$ relative to the plane of the exit opening 33. This angle $\Theta_2$ may generally be in the range of about 1° to about 15°. In some cases, the angle $\Theta_2$ may be about 3°. The angle $\Theta_2$ may be sufficient to provide a directional projection of UV light that is angularly offset toward (or directed toward) the exit opening of the tunnel 32 relative to a plane that is normal to the movement direction of the conveyor 26. In such an instance, this angled directional projection of UV light may direct some of the UV light towards the front side 90 of the object 80 as the front side of the object moves pas the reflector 42 while also directing UV light towards the top side 86 of the object 80. The reflector 42b may be configured to provide a directional projection of UV light that has a direction and a divergence angle such that substantially no UV light (defined as less than 10 percent of the light emission of the corresponding light source) is projected onto the exit opening or the exit opening of the tunnel. "Projected onto" means the light that is projected by the light source/reflector and does not include UV light that may be reflected off of the object or other surfaces in the tunnel.

While the illustrative sanitization tunnel device 10 is shown as having the angularly offset UV light sources 40 positioned along the top side of the tunnel 32, it is contemplated that angularly offset UV light sources 40 may be positioned along any side of the tunnel 32 or any combination of sides of the tunnel 32. For example, the angularly offset UV light sources 40 may be positioned along the bottom side of the tunnel 32. In another example, one angularly offset UV light source 40 may be positioned along the top side of the tunnel 32 while another oppositely angularly offset UV light source 40 may be positioned along the bottom side of the tunnel 32. These are just some examples of possible reflector 42 configurations. It is contemplated that angularly offsetting of at least one reflector 42 towards the entrance opening 34 of the tunnel 32 and at least one reflector 42 towards the exit opening of the tunnel 32, UV light may be projected onto all six sides or faces 82, 84, 86, 88, 90, 92 of the object 80 to be disinfected/sanitized. For example, such an arrangement may allow for the specified UV dosage to be transmitted to all six sides or faces 82, 84, 86, 88, 90, 92 of the object 80 to be disinfected/sanitized. If it further contemplated that such an arrangement may reduce the number of UV lamps and ballasts required (in the range of about ≥60% reduction from some conventional UV sanitization tunnels) to achieve similar dosage levels than when the present reflectors 42 are not provided. Such a reduction in required lamps results in increased energy efficiency (or a reduction in energy usage).

Figure 6:
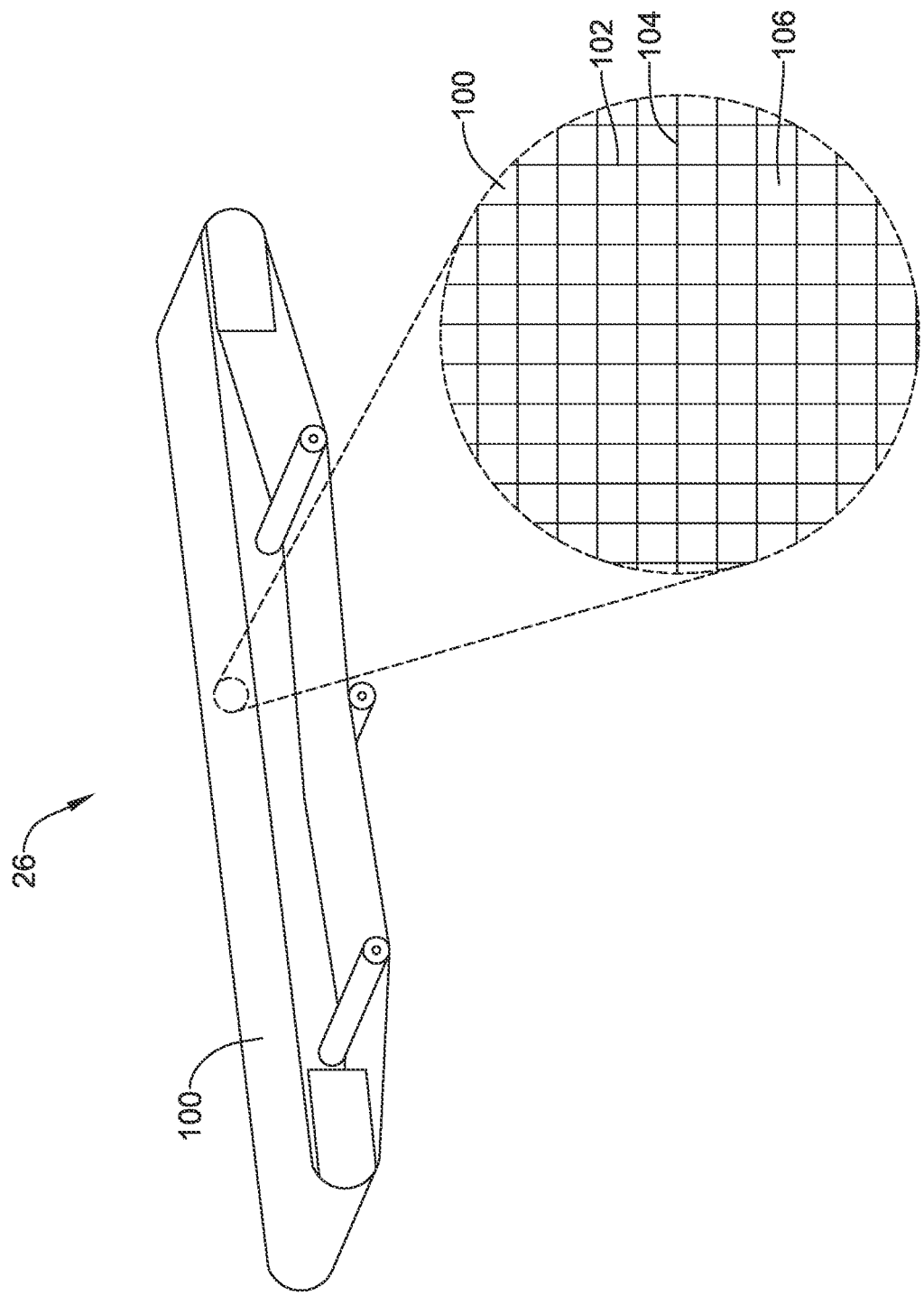
FIG. 6 is a perspective view of an illustrative conveyor belt for use with the illustrative sanitization tunnel device of FIG. 1.

The reflectors 42c, 42d positioned along the bottom side of the tunnel 32 may be placed below the conveyor 26 such that the conveyor 26 is positioned between the reflectors 42c, 42d and the bottom side 88 of the object 80 to be disinfected/sanitized. In some cases, the conveyor 26 may be structured to allow UV light to penetrate the conveyor 26 and contact the bottom side 88 of the object. In some cases, this may be accomplished through material selection and/or a physical configuration of the conveyor 26. FIG. 6 illustrates one example conveyor 26 that may be utilized in the sanitization tunnel device 10. The conveyor 26 includes a conveyor belt 100 made from a porous material. In some cases, the porous material may be a mesh formed from interwoven strands 102, 104. In other cases, the porous material may be formed from a laser cut material. The porous material may be formed such that the openings 106 form at least 80% of the conveyor belt 100 such that UV light may pass to the object 80 to be disinfected/sanitized. Alternatively, or in addition, the conveyor belt 100 may be made from a material that is at least partially transparent to UV light to allow the UV light to pass through the conveyor belt 100 to the object 80.

Figure 7:
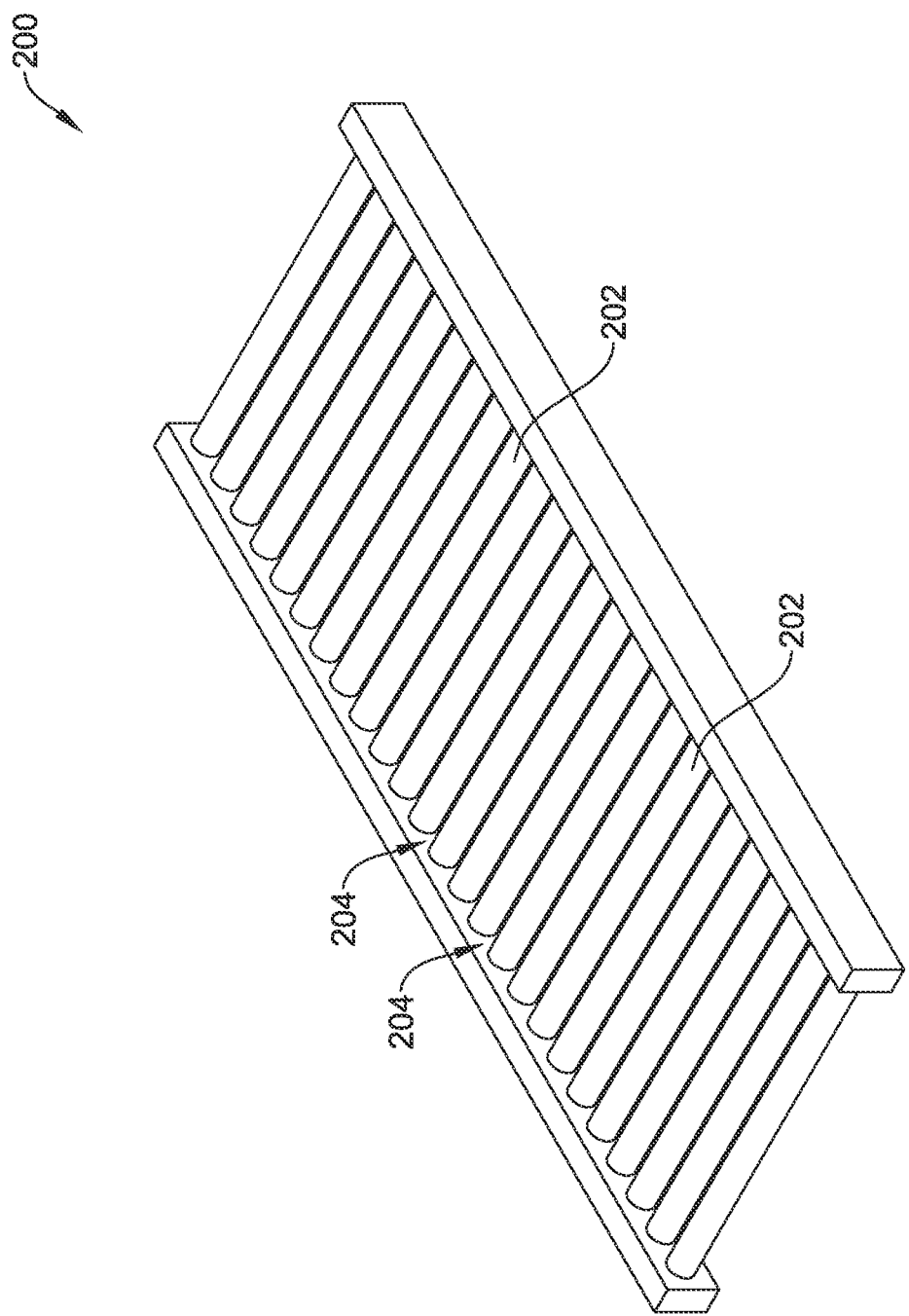
FIG. 7 is a perspective view of another illustrative conveyor for use with the illustrative sanitization tunnel device of FIG. 1.

FIG. 7 illustrates another alternative conveyor 200. The conveyor 200 may include a plurality of rollers 202. In some cases, the rollers 202 may be laterally spaced such that a gap 204 is present between adjacent rollers 202. The gaps 204 may allow UV light to contact the bottom side 88 of the object 80. It is contemplated that as the object 80 moves along the conveyor 200, different portions of the bottom side 88 will be disposed over gaps 204 to allow for disinfection of the bottom side 88. The number of rollers 202 and hence gaps 204 may be determined by the overall length of the conveyor 200, the size of the rollers 202, and/or the desired length of the gaps 204.

Figure 8:
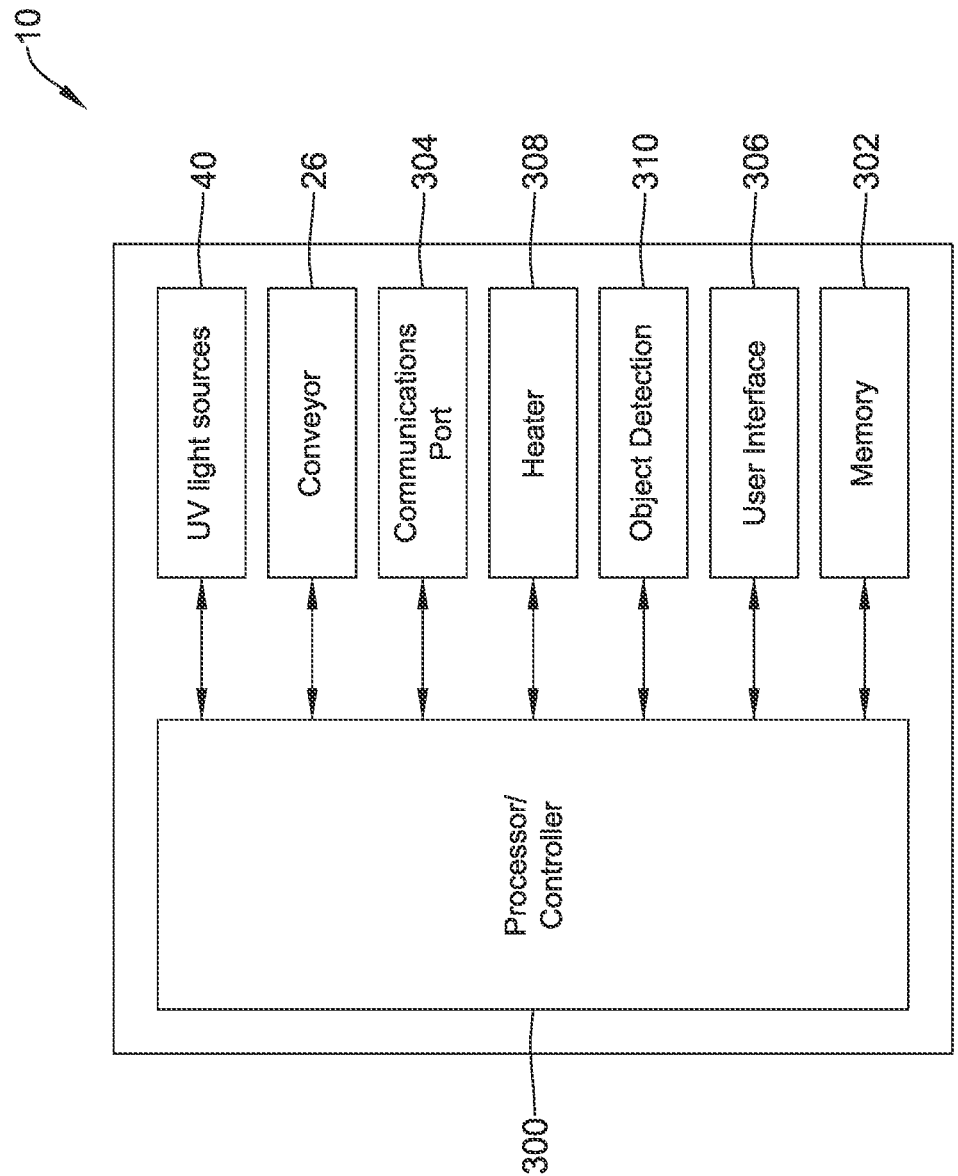
FIG. 8 is a schematic block diagram of the illustrative sanitization tunnel device of FIG. 1.

FIG. 8 is a schematic block diagram of the illustrative sanitization tunnel device 10. The illustrative sanitization tunnel device 10 includes additional components which may improve and/or facilitate the disinfection of objects within the tunnel 32. For example, the sanitization tunnel device 10 may include a controller or processor (e.g., microprocessor, microcontroller, etc.) 300 operatively coupled to the various components thereof, including but not limited to, the UV light sources 40 and/or the conveyor 26. The controller/processor 300 may be configured to control one or more functions of the sanitization tunnel device 10. In some cases, the controller/processor 300 may be mounted to or near the sanitization tunnel device 10. In other cases, the controller/processor 300 may be remotely positioned (e.g., in a control room, in the cloud, etc.). The controller/processor 300 may include a memory 302. In some cases, the memory 302 may be a part of the controller/processor 300. The memory 302 may be in communication with the controller/processor 300. The memory 302 may be used to store any desired information, such as, but not limited to, instructions for operation of the sanitization tunnel device 10 including, but not limited to, control parameters for the various components thereof. In some cases, the memory 302 may store UV light dosage requirements, UV light intensity data, conveyor 26 speed data, algorithms for determining UV light intensity settings and/or conveyor 26 speed, etc. The memory 302 may be any suitable type of storage device including, but not limited to, RAM, ROM, EPROM, flash memory, a hard drive, and/or the like. In some cases, the controller/processor 300 may store information within the memory 302, and may subsequently retrieve the stored information from the memory 302.

The sanitization tunnel device 10 may further include a communications port 304. The communications port 304 may be a wired network interface or a wireless network interface configured to connect the controller/processor 300 and/or the sanitization tunnel device 10 with other devices. The communications port 304 may include a wireless transceiver and other devices configured to communicate with the sanitization tunnel device 10 may include a compatible wireless transceiver. It is contemplated that the wireless transceivers may communicate using a standard and/or a proprietary communication protocol. Suitable standard wireless protocols may include, for example, cellular communication, ZigBee, Bluetooth, WiFi, IrDA, dedicated short range communication (DSRC), EnOcean, or any other suitable wireless protocols, as desired.

The sanitization tunnel device 10 may further include a user interface 306 including a display and a means for receiving user input (e.g., touch screens, buttons, keyboards, etc.). The user interface 306 may be in communication with the controller/processor 300 to allow a user to input control parameters and/or change control operation of the sanitization tunnel device 10 via the controller/processor 300.

While not explicitly shown, the sanitization tunnel device 10 and/or the various components thereof may be coupled to an energy source which provides power thereto.

The sanitization tunnel device 10 may further include one or more heaters 308 operatively coupled to the controller/processor 300. Some illustrative heaters 308 may be include, but are not limited to, resistive heater, blower heaters, etc. The heater 308 may be positioned to heat the air and/or components within the tunnel 32 to provide catalytic disinfection in addition to the UV disinfection by increasing the temperature of the air and/or components within the tunnel 32. In some cases, the heater 308 may be positioned to increase the temperature of the air adjacent to the entrance opening 34 so that the air is warmed as the object enters the tunnel 32. However, this is not required. The controller/processor 300 may be in communication with the heater 308 and configured to turn the heater 308 on/off automatically or in response to a user input (e.g., received via the user interface 306). For example, the controller/processor 300 may be configured to maintain a temperature of the air within the tunnel 32 at about 20° Celsius (C). Alternatively, or additionally, the controller/processor 300 may be configured to control the heater 308 such that the heater 308 raises the temperature of the air within the tunnel 32 by about 3 to 5° C. above ambient.

In some cases, the sanitization tunnel device 10 may include one or more object detection sensors 310 operatively coupled to the controller/processor 300. The object detection sensors 310 may be configured to detect an object to be disinfected/sanitized and/or a size of the object to be disinfected/sanitized. Some illustrative object detection sensors 310 may include, but are not limited to, ultrasound sensors, millimeter wave sensors, object detection cameras, etc. In some cases, the object detection sensor 310 may be positioned to detect the size of an object to be disinfected/sanitized prior to the object entering the tunnel 32. The object detection sensor 310 may be positioned at any suitable location including upstream of the entrance to the tunnel and/or within the tunnel 32. This may allow the controller/processor 300 to control an intensity of the UV light emitted by the UV light sources 40 based on the object size. For example, the controller/processor 300 may increase the intensity of the UV light emitted by the UV light sources 40 for larger objects relative to the objects of a smaller size. In some cases, more than one object detection sensor 310 may be spaced along the conveyor 26 to detect objects at differing locations. For example, an object detection sensor 310 may be positioned at the exit opening of the tunnel 32 to determine when the object is no longer in the tunnel 32 (and thus sanitization is no longer required).

The controller/processor 300 may be configured to issue control commands to the UV light sources 40. In some cases, the controller/processor 300 may be configured to turn at least one of the UV light sources 40 ON and OFF. The ON/OFF commands may be in response to a manual user input, a signal received from the object detection sensor 310, and/or scheduled to occur at predetermined times. In some cases, the controller/processor 300 may be configured to control or set an intensity level of at least one of the UV light sources 40. In some cases, the intensity level of one or more UV light sources 40 may be increased or decreased in response to a signal from the object detection sensor 310. The intensity level of one or more of the UV light sources 40 may be proportional to the size of the object to be disinfected/sanitized. For example, the controller/processor 300 may be configured to reduce an intensity level as a size of the object to be disinfected/sanitized decreases or to increase an intensity level as the size of the object to be disinfected/sanitized increases. It is further contemplated that the controller/processor 300 may be configured to control an intensity level of one more of the UV light sources 40 based on a material of the object to be disinfected/sanitized. It is contemplated that the UV intensity may be increased for objects that are formed from materials more likely to trap pathogens. In some cases, the material of the object may be manually input into the controller/processor 300 by a user at the user interface 306. In other cases, the material of the object may be determined by a sensory input from a sensor or the object detection sensor 310 and communicated to the controller/processor 300.

Alternatively, or additionally, the controller/processor 300 may be configured control the intensity of one or more of the UV light sources 40 based on a speed of the conveyor 26. For example, the controller/processor 300 may be operatively coupled to a motor driving a conveyor belt. Thus, the controller/processor 300 may be able to determine a speed at which the conveyor 26 is moving. Based on the desired UV dosage, the controller/processor 300 may utilize a current conveyor belt speed to adjust the intensity levels of one or more UV light sources 40 to achieve a specified UV light dosage on the object to be disinfected/sanitized. For example, the light output or intensity level of the UV light sources 40 may be adjusted based on the speed of the conveyor 26. Alternatively, or additionally, the controller/processor 300 may be configured to control a speed of the motor driving a conveyor belt, and thus a speed of the conveyor 26, based on the current light output or intensity level of the UV light sources 40 to achieve a desired UV light dosage on the object. Adjusting the light output or intensity level of the UV light sources 40 in this manner may help optimized power utilization and increased UV lamp life.

Figure 9:
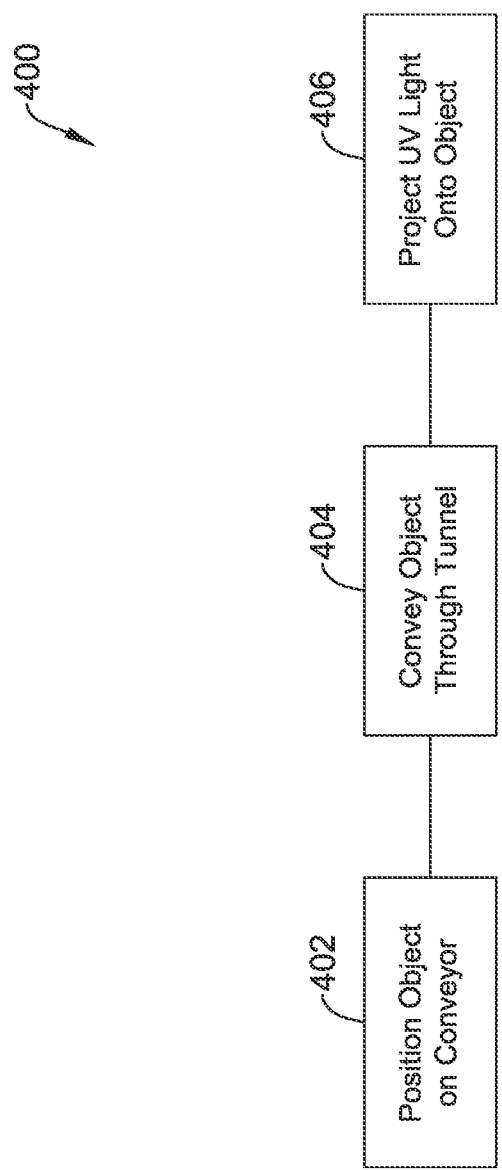
FIG. 9 is an illustrative flow diagram of a method of sanitizing an object.

FIG. 9 is an illustrative flow diagram of an illustrative method 400 for sanitizing and/or disinfecting an object. To begin, the object is placed on the conveyor of the sanitization tunnel device 10, as shown at block 402. The object may then be conveyed via the conveyor 26 through the tunnel 32 of the sanitization tunnel device 10, as shown at block 404. The object may enter the tunnel 32 via the entrance opening 34 and exit via an exit opening 33. As the object travels through the tunnel 32, the object is surrounded by the first lateral side, the second lateral side, the top side, and the bottom side of the tunnel 32. As the object is conveyed through the tunnel, UV light is projected onto the object from a plurality of UV light sources, as shown at block 406. The UV light may have a divergence angle of 45° or less, 20° or less, 10° or less, etc. The UV light may be projected onto the object from each of the first lateral side, the second lateral side, the top side, and the bottom side of the tunnel 32. In some cases, at least some of the projected UV light may be angularly offset toward the exit opening of the tunnel relative to a plane that is normal to a direction of conveyance of the object. Additionally, or alternatively, at least some of the projected UV light may be angularly offset toward the entrance opening of the tunnel relative to a plane that is normal to a direction of conveyance of the object. The UV light is projected such that substantially no UV light (e.g. less than 5 percent of the light emission from the light sources) is projected onto the entrance opening 34 and/or the exit opening 33 of the tunnel 32. "Projected onto" means the light that is projected by the light source/reflector and does not include UV light that may be reflected off of the object or other surfaces in the tunnel. As described herein, as the object is conveyed through the tunnel 32, the tunnel 32 may be heated. The intensity of the UV light and/or the speed of the conveyor 26 may additionally be adjusted or controlled to achieve a desire UV dosage on the object.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A system for sanitizing an object, the system comprising:
   a housing defining a tunnel, the tunnel extending between an entrance opening and an exit opening, the tunnel having a first lateral side, a second lateral side, a top side, and a bottom side;
   a conveyor movable in a first direction to move an object placed on the conveyor through the tunnel from the entrance opening to the exit opening;
   a plurality of ultraviolet (UV) light sources positioned about the tunnel with at least one of the plurality of UV light sources along each of the first lateral side, the second lateral side, the top side, and the bottom side of the tunnel, each of the plurality of UV light sources providing a corresponding UV light emission;
   a plurality of reflectors each extending partially around a corresponding UV light source, each of the plurality of reflectors configured to collect UV light emission from the corresponding UV light source and provide a directional projection of UV light into the tunnel;
   wherein at least one reflector of the plurality of reflectors provides a directional projection of UV light that is angularly offset toward the exit opening of the tunnel relative to a plane that is normal to the first direction of the conveyor; and
   wherein at least one reflector of the plurality of reflectors provides a directional projection of UV light that is angularly offset toward the entrance opening of the tunnel relative to a plane that is normal to the first direction of the conveyor.

2. The system of claim 1, wherein at least one of the plurality of UV light sources is elongated and produces an elongated directional projection of UV light.

3. The system of claim 1, wherein each of the plurality of reflectors are configured to collect UV light emission from a corresponding UV light source and provide a directional projection of UV light that has a divergence angle, wherein the divergence angle is less than 20 degrees.

4. The system of claim 1, wherein each of the plurality of reflectors are configured to provide a directional projection of UV light that does not intersect with the entrance opening or the exit opening of the tunnel.

5. The system of claim 1, wherein at least two of the plurality of UV light sources are positioned along each of the first lateral side, the second lateral side, the top side, and the bottom side of the tunnel.

6. The system of claim 1, wherein at least two of the plurality of UV light sources are spaced from one another in the first direction and positioned along each of the first lateral side, the second lateral side, the top side, and the bottom side of the tunnel.

7. The system of claim 1, further comprising a controller operatively coupled to the plurality of UV light sources, wherein the controller is configured to turn the plurality of UV light sources ON and OFF, and also to set an intensity level of at least one of the plurality of UV light sources.

8. The system of claim 7, wherein the controller is operatively coupled to a motor driving the conveyor, and is configured to control a speed of the motor and thus a speed of the conveyor.

9. The system of claim 8, wherein the controller is configured to control the intensity level of at least one of the plurality of UV light sources based on the speed of the conveyor.

10. The system of claim 7, wherein the controller is configured to control the intensity level of at least one of the plurality of UV light sources based on a size of the object being sanitized.

11. The system of claim 1, further comprising a heater configured to increase a temperature within the tunnel.

12. The system of claim 1, wherein at least one reflector of the plurality of reflectors provides a directional projection of UV light that is angularly offset by an angle in a range of 1° to about 15° toward the exit opening of the tunnel relative to a normal to the first direction of the conveyor.

13. The system of claim 1, wherein at least one reflector of the plurality of reflectors provides a directional projection of UV light that is angularly offset by an angle in a range of 1° to about 15° toward the entrance opening of the tunnel relative to the normal to the first direction of the conveyor.

14. A system for sanitizing an object, the system comprising:
a housing defining a tunnel, the tunnel extending between an entrance opening and an exit opening, the tunnel having a first lateral side, a second lateral side, a top side, and a bottom side;
a conveyor movable in a first direction to move an object placed on the conveyor through the tunnel from the entrance opening to the exit opening;
a plurality of ultraviolet (UV) light source assemblies positioned about the tunnel with at least one of the plurality of UV light source assemblies along each of the first lateral side, the second lateral side, the top side, and the bottom side of the tunnel, each of the plurality of UV light source assemblies providing a corresponding directional projection of UV light into the tunnel;
wherein at least one of the plurality of ultraviolet (UV) light source assemblies provides a directional projection of UV light that is angularly offset toward the exit opening of the tunnel relative to a plane that is normal to the first direction of the conveyor; and
wherein at least one of the plurality of ultraviolet (UV) light source assemblies provides a directional projection of UV light that is angularly offset toward the entrance opening of the tunnel relative to a plane that is normal to the first direction of the conveyor.

15. The system of claim 14, wherein the angularly offset toward the entrance opening of the tunnel is in a range of 1° to about 15°, and the angularly offset toward the exit opening of the tunnel is in a range of 1° to about 15°.

16. The system of claim 14, wherein each of the plurality of ultraviolet (UV) light source assemblies comprise a UV light source and a reflector.

17. The system of claim 14, wherein each of the plurality of ultraviolet (UV) light source assemblies are configured to provide a directional projection of UV light that does not intersect with the entrance opening or the exit opening of the tunnel.

18. The system of claim 14 further comprising a heater configured to increase a temperature within the tunnel.

19. A method for sanitizing an object, the method comprising:
conveying the object through a tunnel, the tunnel having an entrance opening, an exit opening, a first lateral side, a second lateral side, a top side, and a bottom side;
projecting UV light having a divergence angle of less than 10 degrees from each of a plurality of UV light sources onto the object from each of the first lateral side, the second lateral side, the top side, and the bottom side, wherein projecting the UV light includes:
projecting UV light having a divergence angle of less than 10 degrees that is angularly offset toward the exit opening of the tunnel relative to a plane that is normal to a direction of conveyance of the object;
projecting UV light having a divergence angle of less than 10 degrees that is angularly offset toward the entrance opening of the tunnel relative to a plane that is normal to the direction of conveyance of the object; and
wherein substantially no UV light is projected onto the entrance opening or the exit opening of the tunnel.

20. The method of claim 19, further comprising heating the tunnel while sanitizing the object.

* * * * *